US012666654B2

(12) United States Patent
Sung et al.

(10) Patent No.: US 12,666,654 B2
(45) Date of Patent: Jun. 23, 2026

(54) GRAPHENE-BASED BIOSENSOR

(71) Applicant: LG ELECTRONICS INC., Seoul (KR)

(72) Inventors: Jinwoo Sung, Seoul (KR); Jinsan Moon, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 509 days.

(21) Appl. No.: 18/132,562

(22) Filed: Apr. 10, 2023

(65) Prior Publication Data

US 2023/0352597 A1 Nov. 2, 2023

(30) Foreign Application Priority Data

Apr. 27, 2022 (KR) ........................ 10-2022-0051824
Oct. 11, 2022 (WO) ................ PCT/KR2022/015245

(51) Int. Cl.
| | |
|---|---|
| *H10D 30/67* | (2025.01) |
| *G01N 33/543* | (2006.01) |
| *H10D 62/80* | (2025.01) |

(52) U.S. Cl.
CPC ..... *H10D 30/6741* (2025.01); *G01N 33/5438* (2013.01); *H10D 30/6729* (2025.01); *H10D 62/882* (2025.01)

(58) Field of Classification Search
CPC ...... B82Y 15/00; H10K 10/484; H10K 85/20; H10K 85/221; H10K 10/46; H10K 10/462; H10K 10/88; H10D 62/882; H10D 84/82; H10D 30/47
See application file for complete search history.

(56) References Cited

U.S. PATENT DOCUMENTS

| | | | | |
|---|---|---|---|---|
| 7,385,262 B2 * | 6/2008 | O'Keeffe | ............... | H10K 30/65 |
| | | | | 977/749 |
| 8,852,985 B2 * | 10/2014 | Cai | ........................ | G01L 9/0042 |
| | | | | 438/50 |
| 9,029,841 B2 * | 5/2015 | Farmer | ............. | H01L 21/02606 |
| | | | | 257/40 |
| 9,064,842 B2 * | 6/2015 | Bol | .................... | H10D 30/6729 |
| 9,076,873 B2 * | 7/2015 | Chen | .................. | H10D 30/6739 |
| 9,091,648 B2 * | 7/2015 | Afzali-Ardakani | ......................... | |
| | | | | H10K 10/484 |
| 9,276,524 B2 * | 3/2016 | Jenkins | ................ | H10D 62/882 |
| 9,618,474 B2 * | 4/2017 | van Rooyen | .......... | H10D 62/80 |
| 9,679,970 B1 * | 6/2017 | Son | ........................ | H10D 62/882 |
| 9,989,488 B2 * | 6/2018 | Borini | .................... | H10D 30/00 |
| 10,429,342 B2 * | 10/2019 | Hoffman | ............. | H10D 62/882 |
| 10,494,670 B2 * | 12/2019 | van Rooyen | ...... | G01N 27/4146 |
| 10,607,989 B2 * | 3/2020 | Hoffman | ............ | G01N 27/4146 |

(Continued)

*Primary Examiner* — Maliheh Malek

(74) *Attorney, Agent, or Firm* — Birch, Stewart, Kolasch & Birch, LLP

(57) ABSTRACT

The present disclosure relates to a biosensor. The biosensor according to an embodiment of the present disclosure comprises a substrate; a source electrode and a drain electrode on the substrate; a graphene layer on the substrate, and connected to the source electrode and the drain electrode; a first doping layer on an area including one end of the graphene layer; a second doping layer on an area including the other end of the graphene layer and separated from the first doping layer; and a first and a second passivation layer on the first and the second doping layer, respectively. Accordingly, the sensing sensitivity of a graphene-based sensor may be improved.

18 Claims, 7 Drawing Sheets

100

(56)  References Cited

U.S. PATENT DOCUMENTS

| | | | | |
|---|---|---|---|---|
| 10,782,285 B2* | 9/2020 | Taslim | G01N 33/5308 | |
| 10,811,539 B2* | 10/2020 | Van Rooyen | G01N 27/4146 | |
| 10,902,912 B2* | 1/2021 | Tang | H10N 70/823 | |
| 10,968,481 B2* | 4/2021 | van Rooyen | G01N 27/414 | |
| 11,732,296 B2* | 8/2023 | van Rooyen | B01L 3/502715 | |
| | | | | 257/29 |
| 11,908,690 B2* | 2/2024 | Daus | H10D 30/675 | |
| 11,921,112 B2* | 3/2024 | Goldsmith | G01N 27/4146 | |
| 12,055,543 B2* | 8/2024 | Fotouhi | G01N 33/94 | |
| 12,203,923 B2* | 1/2025 | Lim | G01N 27/4145 | |
| 12,247,974 B2* | 3/2025 | Taslim | G01N 33/5308 | |
| 12,455,258 B2* | 10/2025 | Kim | H01R 13/465 | |
| 2009/0140801 A1* | 6/2009 | Ozyilmaz | H10D 62/118 | |
| | | | | 257/29 |
| 2009/0153130 A1* | 6/2009 | Shim | G01N 27/4145 | |
| | | | | 257/253 |
| 2013/0018599 A1* | 1/2013 | Peng | B82Y 15/00 | |
| | | | | 977/734 |
| 2014/0061729 A1* | 3/2014 | Koo | G01N 27/4148 | |
| | | | | 257/253 |
| 2014/0125322 A1* | 5/2014 | Lee | B82Y 15/00 | |
| | | | | 977/734 |
| 2014/0162390 A1* | 6/2014 | Afzali-Ardakani | | |
| | | | | H10K 85/221 |
| | | | | 977/890 |
| 2014/0264467 A1* | 9/2014 | Cheng | G01N 27/4148 | |
| | | | | 257/253 |
| 2014/0295573 A1* | 10/2014 | Huang | G01N 33/54373 | |
| | | | | 422/69 |
| 2015/0038378 A1* | 2/2015 | Cheng | A61B 5/6852 | |
| | | | | 204/403.01 |
| 2015/0069329 A1* | 3/2015 | Jeon | B81C 1/00087 | |
| | | | | 257/29 |
| 2015/0137074 A1* | 5/2015 | Lee | H10D 62/82 | |
| | | | | 257/27 |
| 2015/0243917 A1* | 8/2015 | Kim | C01B 32/194 | |
| | | | | 257/27 |
| 2015/0247819 A1* | 9/2015 | Shi | G01N 33/48735 | |
| | | | | 506/13 |
| 2015/0280011 A1* | 10/2015 | Cho | H10D 30/6757 | |
| | | | | 257/29 |
| 2016/0178569 A1* | 6/2016 | Hoffman | H10D 62/80 | |
| | | | | 257/29 |
| 2016/0265047 A1* | 9/2016 | van Rooyen | G01N 27/4148 | |
| 2017/0018626 A1* | 1/2017 | Hoffman | C12Q 1/6869 | |
| 2017/0053908 A1* | 2/2017 | Hoffman | H10D 62/8303 | |
| 2017/0059514 A1* | 3/2017 | Hoffman | G01N 33/5438 | |
| 2017/0102358 A1* | 4/2017 | Hoffman | H10D 64/254 | |
| 2017/0200909 A1* | 7/2017 | Sonkusale | G01N 27/4146 | |
| 2017/0350882 A1* | 12/2017 | Lin | G01N 33/54353 | |
| 2018/0059051 A1* | 3/2018 | Yang | G01N 33/552 | |
| 2018/0308983 A1* | 10/2018 | Yu | H10D 62/882 | |
| 2018/0313784 A1* | 11/2018 | White | H10D 62/882 | |
| 2019/0181273 A1* | 6/2019 | van Rooyen | C12Q 1/6869 | |
| 2020/0227568 A1* | 7/2020 | Le | H10D 86/60 | |
| 2020/0286959 A1* | 9/2020 | Jin | H10K 85/221 | |
| 2020/0300845 A1* | 9/2020 | Fotouhi | G01N 33/948 | |
| 2020/0350443 A1* | 11/2020 | Lee | H10F 77/331 | |
| 2021/0247409 A1* | 8/2021 | Nawana | G01N 33/5438 | |
| 2021/0328021 A1* | 10/2021 | Hone | H01L 21/041 | |
| 2022/0069243 A1* | 3/2022 | Lefebvre | B82Y 30/00 | |
| 2022/0244217 A1* | 8/2022 | Bockelmann | H10D 30/6741 | |
| 2022/0246430 A1* | 8/2022 | Daus | H01L 21/02568 | |
| 2023/0088634 A1* | 3/2023 | Lin | H10D 30/031 | |
| | | | | 257/288 |
| 2023/0238406 A1* | 7/2023 | Chai | H10F 77/143 | |
| | | | | 257/431 |
| 2023/0329573 A1* | 10/2023 | Choi | G01N 33/48785 | |
| 2023/0329679 A1* | 10/2023 | Lee | A61B 5/0077 | |
| 2023/0330661 A1* | 10/2023 | Lim | G01N 33/48792 | |
| 2023/0330662 A1* | 10/2023 | Kim | G01N 33/48778 | |
| 2023/0333050 A1* | 10/2023 | Kim | H01R 13/465 | |
| 2023/0333085 A1* | 10/2023 | Lim | H01R 12/72 | |
| 2023/0333100 A1* | 10/2023 | Lim | H01R 13/465 | |
| 2024/0182617 A1* | 6/2024 | Lee | G03F 7/038 | |
| 2024/0337544 A1* | 10/2024 | Jung | G01L 1/18 | |
| 2024/0376529 A1* | 11/2024 | Zhang | G01N 27/4146 | |
| 2025/0185388 A1* | 6/2025 | Yoshioka | H10F 77/206 | |
| 2025/0290893 A1* | 9/2025 | Almeida | G01N 33/5438 | |

* cited by examiner

100

100

140a

140b

130

120

GRAPHENE-BASED BIOSENSOR

CROSS REFERENCE TO RELATED APPLICATIONS

This non-provisional application claims the benefit under 35 U.S.C. § 119 (a) to Patent Application Nos. 10-2022-0051824, filed in Republic of Korea on Apr. 27, 2022, and PCT/KR2022/015245, filed in Republic of Korea on Oct. 11, 2022, all of which are hereby expressly incorporated by reference into the present application.

BACKGROUND

1. Field of the Disclosure

The present disclosure relates to a biosensor and, more specifically, to a biosensor capable of improving the sensing sensitivity of a graphene-based sensor.

2. Description of the Related Art

Recently, as diseases having a high infectivity applied, a need for rapid diagnosis and self-diagnosis of the disease in medical fields such as homes, hospitals, and public health centers is increasing.

Therefore, it is required to develop an immunoassay platform with short analysis time and high accuracy without requiring specialized knowledge or complicated procedures.

A biosensor generates an electrical, optical signal, and a color that changes according to a selective reaction between probe material having reactivity for a specific target material contained in a body fluid such as sweat and saliva, or in biological substances such as blood or urine, and the target material. Accordingly, it is possible to check the presence of a specific target material by using the biosensor.

Meanwhile, methods using graphene materials are being studied for the fabrication of biosensors.

A paper entitled "Digital Biosensing by Foundry-Fabricated Graphene Sensors," published in Scientific Reports on Jan. 22, 2009 (hereinafter, it is referred to as 'prior literature'), discloses a method of disposing graphene on a substrate.

However, the prior literature reveals a disadvantage in that electrostatic gating is not performed over the entire graphene channel due to the lattice mismatch between a substrate and a graphene layer, which is caused by a passivation layer covering a part of the graphene layer, and thus the sensing sensitivity is lowered.

SUMMARY

An object of the present disclosure is to provide a biosensor capable of improving the sensing sensitivity of a graphene-based sensor.

Meanwhile, another object of the present disclosure is to provide a biosensor capable of separating a passivation layer from a graphene layer.

To achieve the objects above, a biosensor according to one embodiment of the present disclosure comprises a substrate; a source electrode and a drain electrode separated from each other on the substrate; a graphene layer disposed on the substrate, and including one end connected to the source electrode and the other end connected to the drain electrode; a first doping layer disposed on an area including one end of the graphene layer; a second doping layer disposed on an area including the other end of the graphene layer and separated from the first doping layer; and a first passivation layer and a second passivation layer disposed on the first doping layer and the second doping layer, respectively.

Meanwhile, the first doping layer may be applied on the source electrode and the area including one end of the graphene layer, and the second doping layer may be applied on the drain electrode and the area including the other end of the graphene layer.

To achieve the objects above, a biosensor according to one embodiment of the present disclosure may further include a gate electrode disposed on top of and separated from either of the first passivation layer and the second passivation layer.

Meanwhile, a portion of the graphene layer may be applied by the first doping layer or the second doping layer and by the first passivation layer or the second passivation layer; and the other portion of the graphene layer may be left open without being applied by the first doping layer or the second doping layer and by the first passivation layer or the second passivation layer.

Meanwhile, the source electrode may be formed on a first area which includes the one end of the graphene layer; the first doping layer may be formed on a second area adjacent to the first area of the graphene layer; the doping layer and the passivation layer may not be applied on a third area adjacent to the second area of the graphene layer; the second doping layer may be formed on a fourth area adjacent to the third area of the graphene layer; and the drain electrode may be formed on a fifth area which includes the other end of the graphene layer and is adjacent to the fourth area.

Meanwhile, the length of the second area or the fourth area of the graphene layer may be shorter than a length of the third area.

Meanwhile, the length of the second area or the fourth area of the graphene layer may be less than or equal to 100 nm.

Meanwhile, the length of the second area or the fourth area of the graphene layer may be longer than a length of the first area or the fifth area of the graphene layer.

Meanwhile, as the resistance of the second area or the fourth area of the graphene layer decreases, the conductivity of the graphene layer may increase.

Meanwhile, as the length of the third area of the graphene layer increases, the conductivity of the graphene layer may increase.

Meanwhile, as the ratio of the length of the second area or the fourth area of the graphene layer to the length of the third area of the graphene layer decreases, the conductivity of the graphene layer may increase.

Meanwhile, it is preferable that the height of the graphene layer is less than a height of the substrate.

Meanwhile, as the length of the third area of the graphene layer decreases, the height of the graphene layer may decrease or the height of the first doping layer or the height of the second doping layer may increase.

Meanwhile, the first doping layer or the second doping layer may include an organic compound or an inorganic compound, and the inorganic compound may include at least one of $WO_3$, $MoO_3$, or $ZnO$.

Meanwhile, a biosensor according to one embodiment of the present disclosure may further include an insulating layer disposed on the substrate; and the source electrode, the drain electrode, and the graphene layer may be disposed on the insulating layer.

To achieve the objects above, a biosensor according to another embodiment of the present disclosure comprises a substrate; a source electrode and a drain electrode separated from each other on the substrate; a graphene layer disposed on the substrate, and including one end connected to the source electrode and the other end connected to the drain electrode; a first doping layer and a second doping layer applied on a portion of the graphene layer and separated from each other thereon; and a first passivation layer and a second passivation layer disposed on the first doping layer and the second doping layer, respectively.

Effects of the Disclosure

A biosensor according to one embodiment of the present disclosure comprises a substrate; a source electrode and a drain electrode separated from each other on the substrate; a graphene layer disposed on the substrate, and including one end connected to the source electrode and the other end connected to the drain electrode; a first doping layer disposed on an area including one end of the graphene layer; a second doping layer disposed on an area including the other end of the graphene layer and separated from the first doping layer; and a first passivation layer and a second passivation layer disposed on the first doping layer and the second doping layer, respectively. Accordingly, the sensing sensitivity of a graphene-based sensor may be improved. Also, the passivation layer may be separated from the graphene layer.

Meanwhile, the first doping layer may be applied on the source electrode and the area including one end of the graphene layer, and the second doping layer may be applied on the drain electrode and the area including the other end of the graphene layer. Accordingly, the sensing sensitivity of a graphene-based sensor may be improved.

Meanwhile, a biosensor according to one embodiment of the present disclosure may further include a gate electrode disposed on top of and separated from either of the first passivation layer and the second passivation layer. Accordingly, the sensing sensitivity of a graphene-based sensor may be improved.

Meanwhile, a portion of the graphene layer may be applied by the first doping layer or the second doping layer and the first passivation layer or the second passivation layer; and the other portion of the graphene layer may be left open without being applied by the first doping layer or the second doping layer and the first passivation layer or the second passivation layer. Accordingly, the sensing sensitivity of a graphene-based sensor may be improved. Also, the passivation layer may be separated from the graphene layer.

Meanwhile, the source electrode may be formed on a first area which includes the one end of the graphene layer; the first doping layer may be formed on a second area adjacent to the first area of the graphene layer; the doping layer and the passivation layer may not be applied on a third area adjacent to the second area of the graphene layer; the second doping layer may be formed on a fourth area adjacent to the third area of the graphene layer; and the drain electrode may be formed on a fifth area which includes the other end of the graphene layer and is adjacent to the fourth area. Accordingly, the sensing sensitivity of a graphene-based sensor may be improved. Also, the passivation layer may be separated from the graphene layer.

Meanwhile, the length of the second area or the fourth area of the graphene layer may be shorter than a length of the third area. Accordingly, the sensing sensitivity of a graphene-based sensor may be improved.

Meanwhile, the length of the second area or the fourth area of the graphene layer may be less than or equal to 100 nm. Accordingly, the sensing sensitivity of a graphene-based sensor may be improved.

Meanwhile, the length of the second area or the fourth area of the graphene layer may be longer than a length of the first area or the fifth area of the graphene layer. Accordingly, the sensing sensitivity of a graphene-based sensor may be improved.

Meanwhile, as the resistance of the second area or the fourth area of the graphene layer decreases, the conductivity of the graphene layer may increase. Accordingly, the sensing sensitivity of a graphene-based sensor may be improved.

Meanwhile, as the length of the third area of the graphene layer increases, the conductivity of the graphene layer may increase. Accordingly, the sensing sensitivity of a graphene-based sensor may be improved.

Meanwhile, as the ratio of the length of the second area or the fourth area of the graphene layer to the length of the third area of the graphene layer decreases, the conductivity of the graphene layer may increase. Accordingly, the sensing sensitivity of a graphene-based sensor may be improved.

Meanwhile, it is preferable that the height of the graphene layer is less than a height of the substrate. Accordingly, the sensing sensitivity of a graphene-based sensor may be improved.

Meanwhile, as the length of the third area of the graphene layer decreases, the height of the graphene layer may decrease or the height of the first doping layer or the height of the second doping layer may increase. Accordingly, the sensing sensitivity of a graphene-based sensor may be improved.

Meanwhile, the first doping layer or the second doping layer may include an organic compound or an inorganic compound, and the inorganic compound may include at least one of $WO_3$, $MoO_3$, or $ZnO$. Accordingly, the sensing sensitivity of a graphene-based sensor may be improved.

Meanwhile, a biosensor according to one embodiment of the present disclosure may further include an insulating layer disposed on the substrate; and the source electrode, the drain electrode, and the graphene layer may be disposed on the insulating layer. Accordingly, the sensing sensitivity of a graphene-based sensor may be improved.

A biosensor according to another embodiment of the present disclosure comprises a substrate; a source electrode and a drain electrode separated from each other on the substrate; a graphene layer disposed on the substrate, and including one end connected to the source electrode and the other end connected to the drain electrode; a first doping layer and a second doping layer applied on a portion of the graphene layer and separated from each other thereon; and a first passivation layer and a second passivation layer disposed on the first doping layer and the second doping layer, respectively. Accordingly, the sensing sensitivity of a graphene-based sensor may be improved. Also, the passivation layer may be separated from the graphene layer.

DETAILED DESCRIPTION OF THE PREFERRED EMBODIMENTS

In what follows, the present disclosure will be described in more detail with reference to appended drawings.

The suffixes "module" and "unit" for the constituting elements used in the following descriptions are assigned only for the convenience of writing the present disclosure and do not have separate meanings or roles distinguished from each other. Therefore, the "module" and "unit" may be used interchangeably.

In the present specification, target materials are biomaterials representing a specific substrate, and are interpreted as having the same meaning as analytical bodies or analytes. In the present embodiment, the target material may be an antigen. In the present specification, probe material is a biomaterial that specifically binds to a target material and is interpreted as having the same meaning as a receptor or an acceptor. In the present embodiment, the probe material may be an antibody.

The electrochemical-based biosensor combines the analytical ability of the electrochemical method with a specificity of biological recognition and detects a biological recognition phenomenon for a target material as a change in current or potential, by immobilizing or containing a material having biological specificity, i.e., probe material such as an enzyme, an antigen, an antibody, or a biochemical material, on the surface of an electrode.

Figure 1:
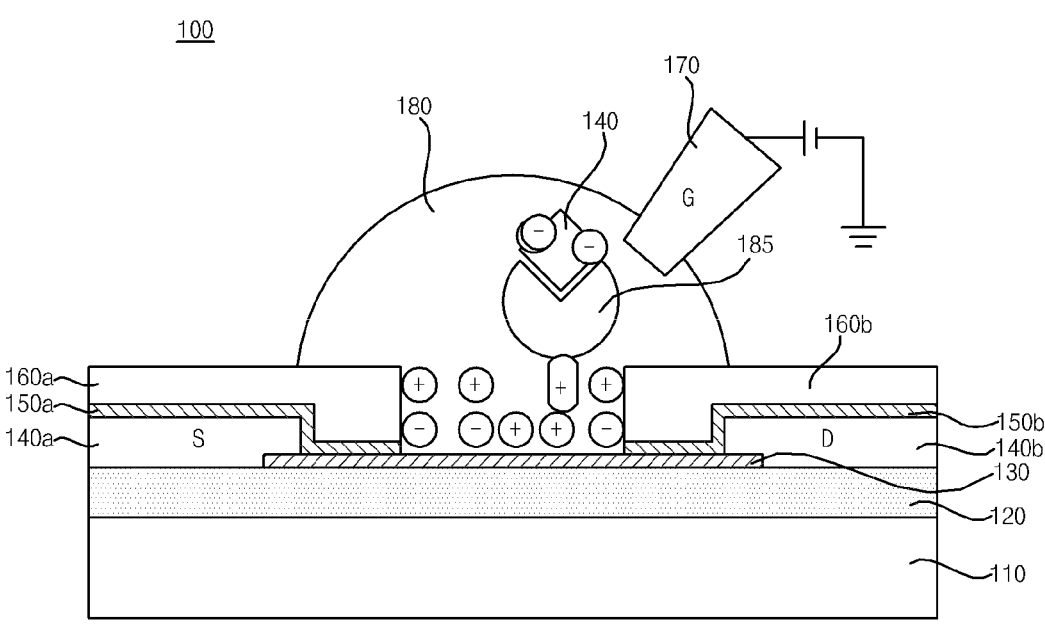
FIG. 1 is one example of a side view of a biosensor according to one embodiment of the present disclosure.
Figure 2A:
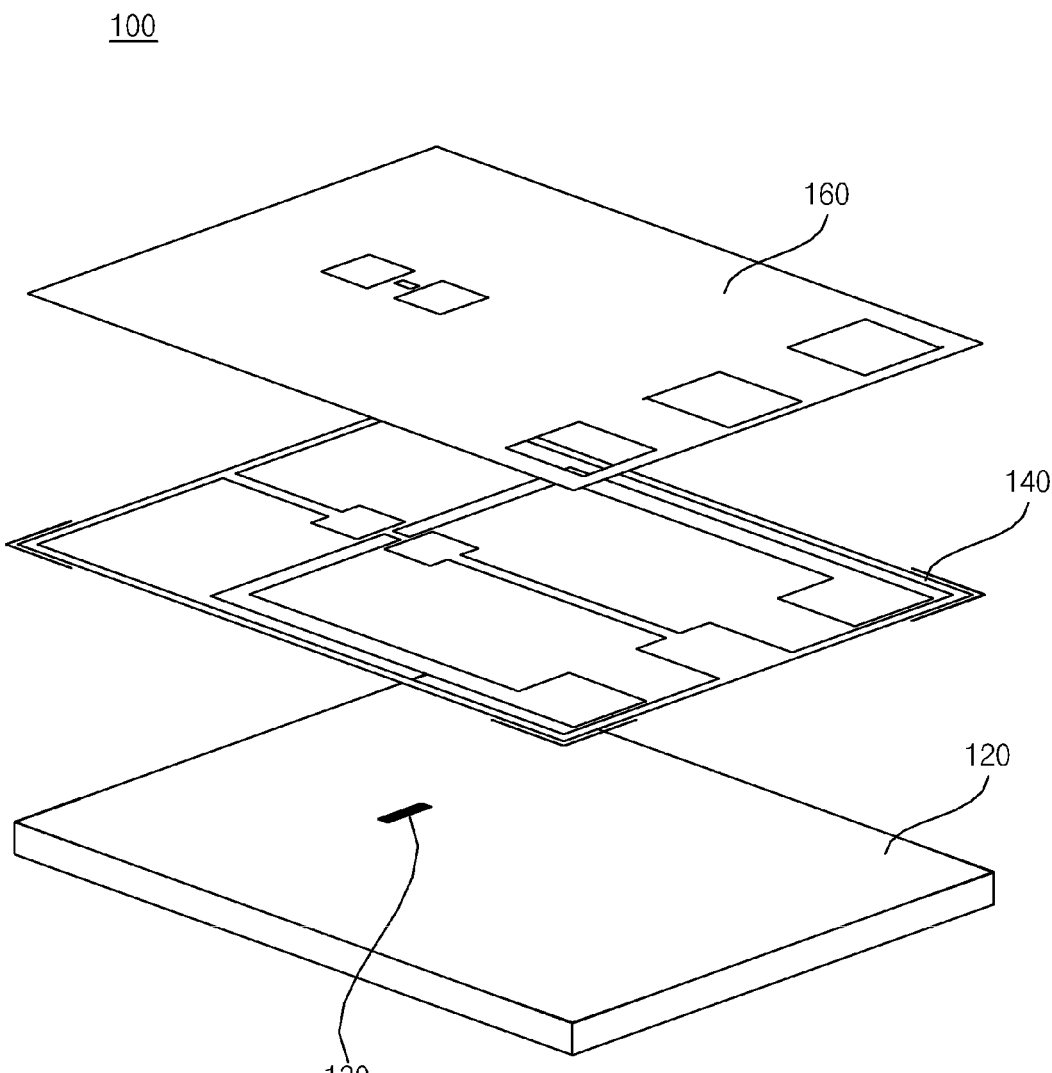
FIG. 2a is a simplified perspective view of the biosensor of FIG. 1.
Figure 2B:
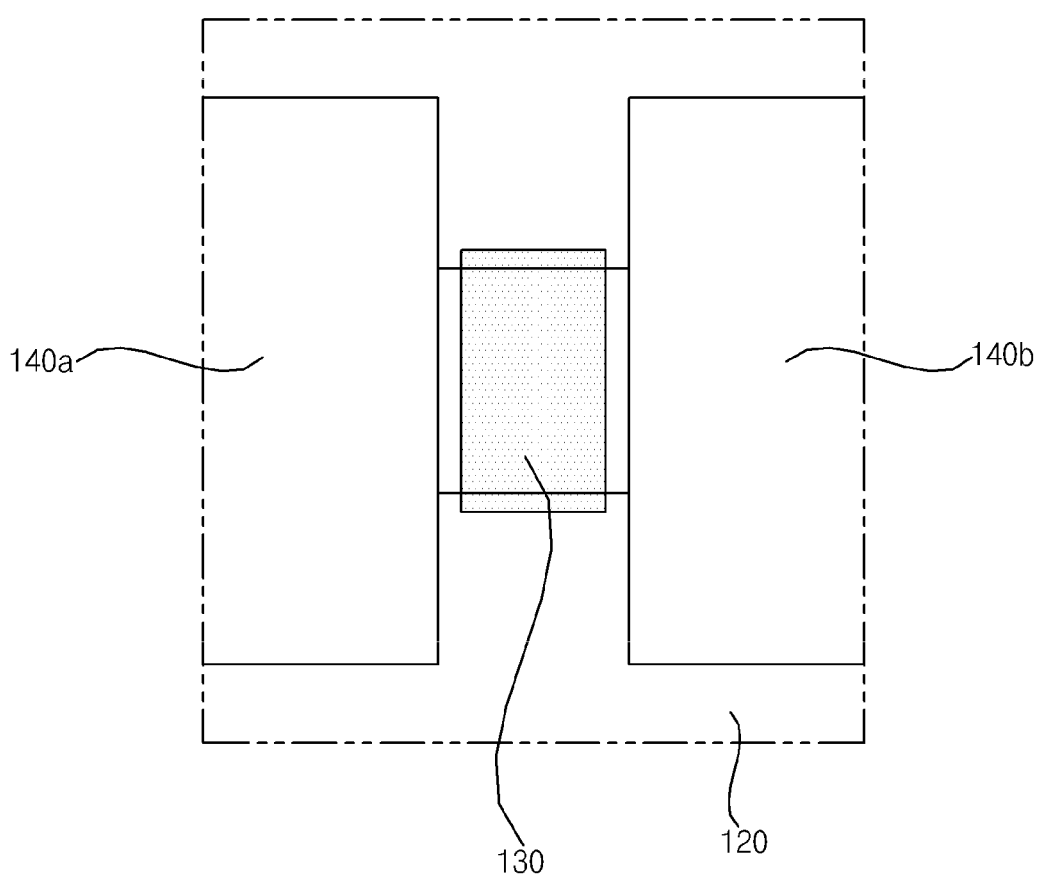
FIG. 2b is one example of a top view of the biosensor of FIG. 1.

FIG. 1 is one example of a side view of a biosensor according to one embodiment of the present disclosure, FIG. 2*a* is a simplified perspective view of the biosensor of FIG. 1, and FIG. 2*b* is one example of a top view of the biosensor of FIG. 1.

Referring to the figure, the biosensor 100 according to one embodiment of the present disclosure includes a graphene-based field effect transistor (FET) using the graphene layer 130 as a channel.

To this configuration, the biosensor 100 according to one embodiment of the present disclosure comprises a substrate 110; a source electrode 140*a* and a drain electrode 140*b* separated from each other on the substrate 110; a graphene layer 130 disposed on the substrate 110, and including one end connected to the source electrode 140*a* and the other end connected to the drain electrode 140*b*; a first doping layer 150*a* disposed on an area including one end of the graphene layer 130; a second doping layer 150*b* disposed on an area including the other end of the graphene layer 130 and separated from the first doping layer 150*a*; and a first passivation layer 160*a* and a second passivation layer 160*b* disposed on the first doping layer 150*a* and the second doping layer 150*b*, respectively.

According to the biosensor 100 of one embodiment of the present disclosure, the passivation layers 160*a* and 160*b* and the graphene layer 130 are separated from each other. Accordingly, a lattice mismatch between the substrate 110 and the graphene layer 130 is significantly reduced, eventually improving graphene-based sensing sensitivity.

Meanwhile, the biosensor 100 according to one embodiment of the present disclosure may further include a gate electrode 170 disposed on top of and separated from either of the first passivation layer 160*a* and the second passivation layer 160*b*. Accordingly, the sensing sensitivity of a graphene-based sensor may be improved.

Meanwhile, the biosensor 100 according to one embodiment of the present disclosure further includes an insulating layer 120 disposed on the substrate 110.

In other words, the source electrode 140*a*, the drain electrode 140*b*, and the graphene layer 130 may be disposed on the insulating layer 120. Accordingly, the sensing sensitivity of a graphene-based sensor may be improved.

Meanwhile, a biosensor 100 according to another embodiment of the present disclosure comprises a substrate 110; an insulating layer 120 on the substrate 110, a graphene layer 130 disposed on a portion on the insulating layer 120, a source electrode 140*a* disposed on one end of the graphene layer 130 and the insulating layer 120, a drain electrode 140*b* disposed on the other end of the graphene layer 130 and the insulating layer 120, a first doping layer 150*a* disposed on an area including one end of the graphene layer 130, a second doping layer 150*b* disposed on an area including the other end of the graphene layer 130 and separated from the first doping layer 150*a*, and a first passivation layer 160*a* and the second passivation layer 160*b* disposed on the first doping layer 150*a* and the second doping layer 150*b*, respectively.

Meanwhile, the substrate 110 is a semiconductor substrate, which may be made up of a silicon substrate. Meanwhile, the insulating layer 120 on the substrate 110 may be formed of silicon oxide ($SiO_2$) or silicon nitride. For example, a silicon oxide-based insulating layer 120 may be formed on the surface through heat treatment.

Meanwhile, the graphene layer 130 is formed on the insulating layer 120.

For sensing, a portion of the graphene layer 130 is open, and other areas are covered by the doping layers 150*a* and 150*b* and the passivation layers 160*a*, 160*b*.

Meanwhile, the graphene layer 130 may be formed in plurality in the biosensor 100.

Meanwhile, the graphene layer 130 is formed in a portion of the insulating layer 120.

Meanwhile, the source electrode 140*a* and the drain electrode 140*b* are spaced apart from each other and formed on a portion of the insulating layer 120 and the graphene layer 130.

The figure illustrates a case in which the source electrode 140*a* is formed on the left area of the insulating layer 120 and one end of the graphene layer 130, and the drain electrode 140*b* is formed on the right area of the insulating layer 120 and the other end of the graphene layer 130.

The source electrode 140*a* and the drain electrode 140*b* may be formed into the same layer. Accordingly, the source electrode 140*a* and the drain electrode 140*b* may be formed into the same layer through the same process.

For example, the source electrode 140*a* and the drain electrode 140*b* may be formed respectively by forming electrode layers and patterning the corresponding electrode layers simultaneously.

Meanwhile, in addition to the source electrode 140*a* and the drain electrode 140*b*, the gate electrode 170 may also be formed into the same layer through the same process.

As described above, by simultaneously forming the source electrode 140*a*, the drain electrode 140*b*, and the gate electrode 170 that do not overlap with each other, it is possible to reduce the number of process steps and process time and cost.

The source electrode 140*a*, the drain electrode 140*b*, and the gate electrode 170 may include at least one of, but not limited to, Ni, Zn, Pd, Ag, Cd, Pt, Ga, In, and Au.

Meanwhile, the gate electrode 170 is formed being separated from the source electrode 140*a* and the drain electrode 140*b*.

In particular, as shown in the figure, the gate electrode 170 may be disposed on top of and separated from either of the first passivation layer 160*a* and the second passivation layer 160*b*.

The gate electrode 170 may have a larger area than the source electrode 140*a* and the drain electrode 140*b*.

Meanwhile, after forming the source electrode 140*a* and the drain electrode 140*b*, the prior literature forms the passivation layers 160*a*, 160*b* on the source electrode 140*a* and the drain electrode 140*b*; however, in the embodiment of the present disclosure, doping layers 150*a*, 150*b* are formed before the passivation layers 160*a*, 160*b* are formed.

Specifically, the first doping layer 150*a* is applied on an area including the source electrode 140*a* and one end of the graphene layer 130, and the second doping layer 150*b* is applied on the drain electrode 140*b* and one end of the graphene layer 130.

Accordingly, the graphene layer 130 and the passivation layers 160*a*, 160*b* applied subsequently are separated from each other.

Accordingly, a lattice mismatch between the substrate 110 and the graphene layer 130 is significantly reduced, eventually improving graphene-based sensing sensitivity.

Meanwhile, the first doping layer 150*a* or the second doping layer 150*b* may include an organic compound or an inorganic compound, and the inorganic compound may include at least one of WO3, MoO3, or ZnO. Accordingly, it is possible to improve the sensing sensitivity of a graphene-based sensor.

Next, a first passivation layer 160*a* and a second passivation layer 160*b* are applied on the first doping layer 150*a* and the second doping layer 150*b*, respectively.

Meanwhile, a portion in the left part of the graphene layer 130 is applied by the first doped layer 150*a* and the first passivation layer 160*a*, and a portion in the right part of the graphene layer 130 is applied with the second doped layer 150*b* and a second passivation layer 160*b*.

Then, the central portion of the graphene layer 130 is left open and exposed to the outside without being applied by the first doped layer 150*a* or the second doped layer 150*b* and by the first passivation layer 160*a* or the second passivation layer 160*b*.

The passivation layers 160*a*, 160*b* may be formed of a material resistant to moisture to protect the source electrode 140*a* and the drain electrode 140*b*. For example, the passivation layers may be formed of an oxide layer, a nitride layer, or a carbide layer.

Also, the passivation layers 160*a*, 160*b* may be applied as, but are not limited to, polymer resin.

Meanwhile, a specimen solution 180 may contact an open area of the graphene layer 130 and a portion of the gate electrode 170 of the biosensor 100 according to the present embodiment.

The specimen solution 180 is an ionic solution and includes a sensing material 185 that reacts explicitly to a target material 140 to be sensed by the biosensor 100.

For example, when the target material 140 is an antigen, an antibody may be attached to the sensing material 185, and when the target material 140 is an antibody, an antigen may be attached to the sensing material 185.

Meanwhile, a linker material (not shown in the figure) may be attached for a smooth connection between the sensing material 185 and the graphene layer 130. The linker material may be different depending on the graphene layer 130 and the sensing material 185.

When the graphene layer 130 is a polymer structure in the nanoscale, the linker material may be formed of at least one of polyurethane, polydimethylsiloxane, Norland Optical Adhesives (NOA), epoxy, polyethylene terephthalate, polymethyl methacrylate, polyimide, polystyrene, polyethylene naphthalate, polycarbonate, or a combination thereof.

In addition, the linker material may be formed of a combination of polyurethane and NOA (e.g. NOA 68). However, the linker material is not limited thereto, and may be made of various polymers having flexibility.

Meanwhile, when the target material 140 is present in the specimen solution 180 while the specimen solution 180 is applied, and relevant voltages are introduced to the source electrode 140*a*, the drain electrode 140*b*, and the gate electrode 170, respectively, the target material 140 interacts with a sensing material 185, which charges the graphene layer 130 with specific carriers. Accordingly, a depletion state in which charges are accumulated in the graphene layer 130 proceeds, and a drain current flowing through the drain electrode 140*b* increases.

Here, the number of accumulated charges may be proportional to the area of the graphene layer 130. Accordingly, when there are a plurality of graphene layers 130, the drain current flowing through the drain electrode 140*b* is amplified.

Meanwhile, when the target material 140 does not exist in the specimen solution 180 while the specimen solution 180 is applied, and relevant voltages are introduced to the source electrode 140*a*, the drain electrode 140*b*, and the gate electrode 170, respectively, the drain current flows through the drain electrode 140*b* at a significantly lower level than the drain current when the target material 140 exists.

Meanwhile, the specimen solution 180 may refer to a biological material, such as a solution diluted by saliva, a body fluid including sweat, blood, serum, or plasma.

Meanwhile, the biosensor 100 may have various sizes depending on the type of target material, the number of target materials, and the size of the cartridge 100; for example, the biosensor 100 may be designed to have a size of 6*6 mm or 6*8 mm.

Figure 3:
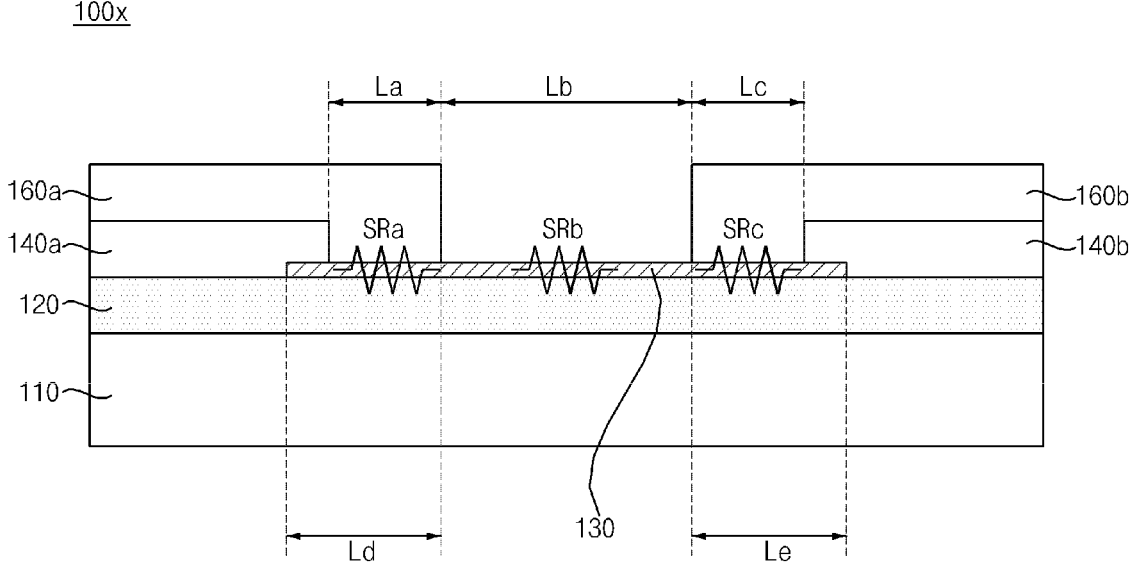
FIG. 3 is one example of a side view of a biosensor related to the present disclosure.

FIG. 3 is one example of a side view of a biosensor related to the present disclosure.

Referring to the figure, the biosensor 100*x* related to the present disclosure comprises a substrate 110, an insulating layer 120 on the substrate 110, a graphene layer 130 disposed on a portion of the insulating layer 120, a source electrode 140*a* disposed on one end of the graphene layer 130 and on the insulating layer 120, a drain electrode 140*b* disposed on the other end of the graphene layer 130 and on the insulating layer 120, a first passivation layer 160*a* disposed on the source electrode 140*a*, and a second passivation layer 160*b* disposed on the drain electrode 140*b*.

According to the structure of FIG. 3, the passivation layers 160*a*, 160*b* and the graphene layer 130 contact in some areas La, Lc.

The figure illustrates a case in which a portion La in the left part Ld of the graphene layer 130 is applied by the first passivation layer 160*a*, and a portion Lc in the right part Le of the graphene layer 130 is applied by the second passivation layer 160*b*.

Accordingly, only the central part Lb of the graphene layer 130 is subjected to resistance modulation; however, the portion La of the graphene layer 130 applied by the first passivation layer 160*a* and the portion Lc of the graphene layer 130 applied by the second passivation layer are not subjected to resistance modulation.

Therefore, the total resistance of the graphene layer 130 is obtained by a sum of the resistance component SRa of a portion La of the graphene layer 130, the resistance component SRc of a portion Lb of the graphene layer 130, and the resistance component SRb of the central portion Lb of the graphene layer 130.

For example, when the resistance component SRa of the portion La of the graphene layer 130 and the resistance component SRc of the portion Lb of the graphene layer 130 are of low resistance, all the resistance components are reflected through channel modulation even if the resistance component SRb of the central portion Lb of the graphene layer 130 is converted from low resistance to high resistance.

Specifically, when the resistance component SRa of the portion La of the graphene layer 130 and the resistance component SRc of the portion Lb of the graphene layer 130 are 1 KΩ, respectively, and the resistance component SRb of the central portion Lb of the graphene layer 130 ranges from 1 to 10 KΩ, the total resistance of the graphene layer 130 is converted to a value between approximately 3 KΩ and 12 kΩ. Accordingly, the sensitivity at the time of sensing is improved.

As another example, when the resistance component SRa of the portion La of the graphene layer 130 and the resistance component SRc of the portion Lb of the graphene layer 130 are of high resistance, a disadvantage is caused in that not all the resistance components are reflected through channel modulation even if the resistance component SRb of the central portion Lb is converted from low resistance to high resistance.

Specifically, when the resistance component SRa of the portion La of the graphene layer 130 and the resistance component SRc of the portion Lb of the graphene layer 130 are 10 KΩ, respectively, and the resistance component SRb of the central portion Lb of the graphene layer 130 ranges from 1 to 10 KΩ, the total resistance of the graphene layer 130 is converted to a value between approximately 21 KΩ and 30 kΩ. Accordingly, the sensitivity at the time of sensing decreases significantly.

Thus, it is preferable that the lengths of the portion La of the graphene layer 130 and the portion Lb of the graphene layer 130 are kept to be less than 100 nm for the resistance component SRa of the portion La of the graphene layer 130 and the resistance component SRc of the portion Lb of the graphene layer 130 to have low resistance.

However, it may be difficult to implement a fabrication process that may form the lengths of the portion La of the graphene layer 130 and the portion Lb of the graphene layer 130 to be smaller than 100 nm.

Accordingly, the present disclosure forms a first doping layer 150a and a second doping layer 150b so that the resistance component SRa of the portion La of the graphene layer 130 and the resistance component SRc of the portion Lb of the graphene layer 130 have low resistance. For the doping layers, refer to the description of the biosensor 100 of FIG. 1.

Figure 4:
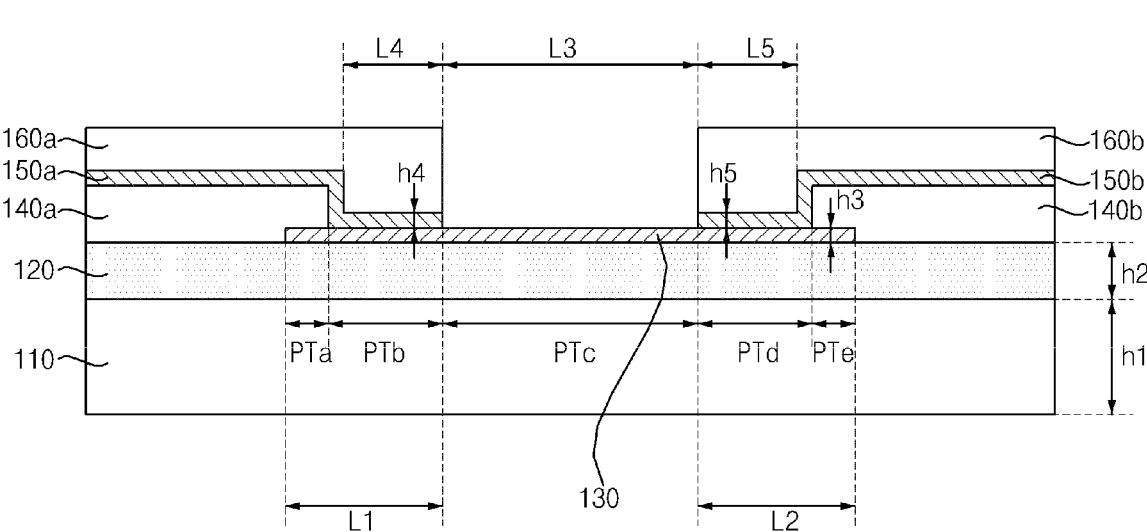
FIGS. 4 to 6 are side views of a biosensor according to various embodiments of the present disclosure.
Figure 5:
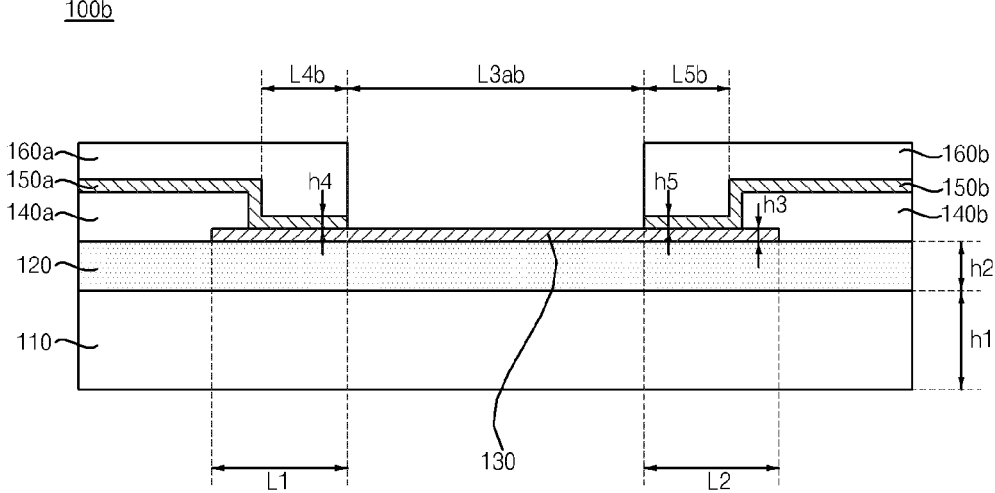
Figure 6:
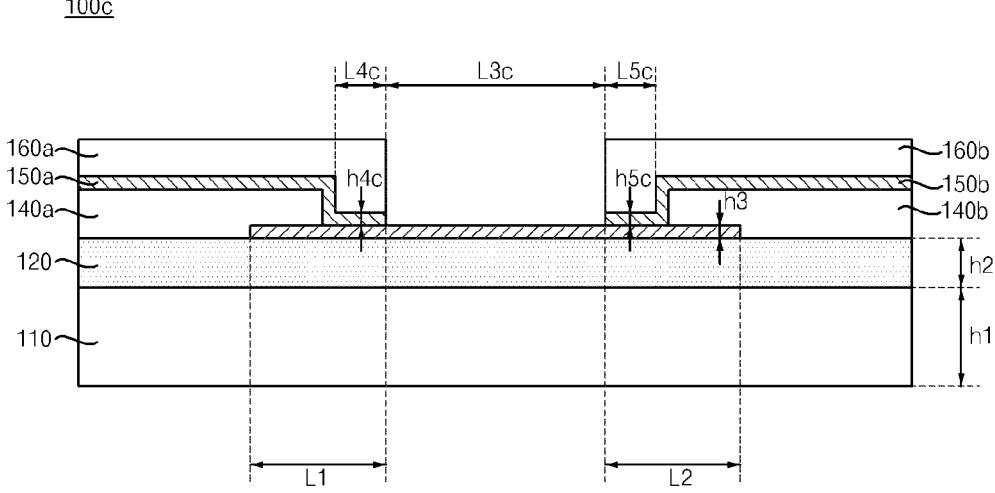

FIGS. 4 to 6 are side views of a biosensor according to various embodiments of the present disclosure.

FIG. 4 is a drawing referenced to describe the biosensor according to one embodiment of the present disclosure of FIG. 1.

Referring to the figure, the biosensor 110a according to one embodiment of the present disclosure comprises a substrate 110; a source electrode 140a and a drain electrode

140b separated from each other on the substrate 110; a graphene layer 130 disposed on the substrate 110, and including one end connected to the source electrode 140a and the other end connected to the drain electrode 140b; a first doping layer 150a disposed on an area including one end of the graphene layer 130; a second doping layer 150b disposed on an area including the other end of the graphene layer 130 and separated from the first doping layer 150a; and a first passivation layer 160a and a second passivation layer 160b disposed on the first doping layer 150a and the second doping layer 150b, respectively.

Meanwhile, the source electrode 140a may be formed on a first area PTa including one end of the graphene layer 130, the first doping layer 150a may be formed on a second area PTb adjacent to the first area PTa of the graphene layer 130, a third area PTc adjacent to the second area PTb of the graphene layer 130 may not be applied with the doping layer 150 and the passivation layers 160a, 160b, the second doping layer 150b may be formed on a fourth area PTd adjacent to the third area PTc of the graphene layer 130, and the drain electrode 140b may be formed on a fifth area PTe which includes the other end of the graphene layer 130 and is adjacent to the fourth area PTd. Accordingly, the sensing sensitivity of a graphene-based sensor may be improved.

The figure illustrates a case in which the source electrode 140a is formed on the first area PTa excluding the L4 area in the left part L1 of the graphene layer 130, and the drain electrode 140b is formed on the fifth area PTe excluding the L5 area in the right part of the graphene layer 130.

The figure illustrates that the first doping layer 150a is formed on the second area PTb of the graphene layer 130 corresponding to the L4 area, the second doping layer 150b is formed on the fourth area PTd corresponding to the L5 area, and the third area PTc of the graphene layer 130 corresponding to the L3 area is made open. Accordingly, the passivation layers 160a, 160b may be separated from the graphene layer 130.

Meanwhile, since the first doping layer 150a is formed on the second area PTb of the graphene layer 130 corresponding to the L4 area, and the second doping layer 150b is formed on the fourth area PTd corresponding to the L5 area, the resistance component of the second area PTb of the graphene layer 130 corresponding to the L4 area and the resistance component of the fourth area PTd corresponding to the L5 area exhibit a considerably low resistance value.

Accordingly, since the resistance component of the second area PTb of the graphene layer 130 corresponding to the L4 area and the resistance component of the fourth area PTd corresponding to the L5 area become small, all the resistance components are reflected through channel modulation even if the resistance component of the central area L2 of the graphene layer 130 is converted from low resistance to high resistance.

Specifically, when the resistance component of the second area PTb of the graphene layer 130 corresponding to the L4 area and the resistance component of the fourth area PTd corresponding to the L5 area are 1 KΩ, respectively, and the resistance component of the central area L2 of the graphene layer 130 ranges from 1 to 10 KΩ, the total resistance of the graphene layer 130 is converted to a value between approximately 3 KΩ and 12 kΩ. Accordingly, the sensitivity at the time of sensing is improved.

Meanwhile, it is preferable that the length L4 of the second area PTb or the length L5 of the fourth area PTd of the graphene layer 130 is shorter than the length L3 of the third area PTc. Accordingly, since the resistance component of the second area PTb or the fourth area PTd of the graphene layer 130 decreases, the sensing sensitivity of a graphene-based sensor may be eventually improved.

Meanwhile, it is preferable that the length L4 of the second area PTb or the length L5 of the fourth area PTd of the graphene layer 130 is less than 100 nm. Accordingly, since the resistance component of the second area PTb or the fourth area PTd of the graphene layer 130 decreases, the sensing sensitivity of a graphene-based sensor may be eventually improved.

Meanwhile, it is preferable that the length L4 of the second area PTb or the length L5 of the fourth area PTd of the graphene layer 130 is longer than the length L1-L4 of the first area PTa or the length L2-L5 of the fifth area PTe of the graphene layer 130. Accordingly, the sensing sensitivity of a graphene-based sensor may be improved.

Meanwhile, as the resistance value of the second area PTb or the fourth area PTd of the graphene layer 130 decreases, the conductivity of the graphene layer 130 may increase. Accordingly, since the resistance component of the third area PTc of the graphene layer 130 acts as a primary factor, the sensing sensitivity of a graphene-based sensor may be improved eventually.

Meanwhile, as the length L3 of the third area PTc of the graphene layer 130 increases, the conductivity of the graphene layer 130 may increase. Accordingly, since the resistance component of the third area PTc of the graphene layer 130 acts as a primary factor, the sensing sensitivity of a graphene-based sensor may be improved eventually.

Meanwhile, as the ratio of the length L4 of the second area PTb or the length L5 of the fourth area PTd of the graphene layer 130 to the length L3 of the third area PTc of the graphene layer 130 decreases, the conductivity of the graphene layer 130 may increase. Accordingly, since the resistance component of the second area PTb or the fourth area PTd of the graphene layer 130 decreases, the sensing sensitivity of a graphene-based sensor may be improved eventually.

Meanwhile, it is preferable that the height h3 of the graphene layer 130 is smaller than the height h1 of the substrate 110 and smaller than the height h2 of the insulating layer 120.

Meanwhile, as the length of the third area PTc of the graphene layer 130 decreases, it is preferable that the height h3 of the graphene layer 130 decreases, the height h4 of the first doping layer 150a increases, or the height h5 of the second doping layer 150b increases. Accordingly, since the resistance component of the third area PTc of the graphene layer 130 acts as a primary factor, the sensing sensitivity of a graphene-based sensor may be improved eventually.

FIG. 5 is one example of a side view of a biosensor according to another embodiment of the present disclosure.

Referring to the figure, the biosensor 100b according to another embodiment of the present disclosure comprises a substrate 110; a source electrode 140a and a drain electrode 140b separated from each other on the substrate 110; a graphene layer 130 disposed on the substrate 110, and including one end connected to the source electrode 140a and the other end connected to the drain electrode 140b; a first doping layer 150a disposed on an area including one end of the graphene layer 130; a second doping layer 150b disposed on an area including the other end of the graphene layer 130 and separated from the first doping layer 150a; and a first passivation layer 160a and a second passivation layer 160b disposed on the first doping layer 150a and the second doping layer 150b, respectively.

Compared with the biosensor 100a of FIG. 4, the biosensor 100b of FIG. 5 is different in that the first doping layer 150a is formed in the L4b area on the graphene layer 130, where L4b area is smaller than L4 of FIG. 4; the second doping layer 150b is formed in the L5b area on the graphene layer 130, where L5b area is smaller than L5 of FIG. 4; and the open area of the graphene layer 130 is L3ab, which is larger than L3 of FIG. 4.

As shown in FIG. 5, as the length of the third area PTc of the graphene layer 130 increases, the influence of the resistance component due to the area of the graphene layer 130 on which the first doping layer 150a is formed and the resistance component due to the area of the graphene layer 130 on which the second doping layer 150b decreases, and thus, the conductivity of the graphene layer 130 may increase. Accordingly, the sensing sensitivity of a graphene-based sensor may be improved.

FIG. 6 is one example of a side view of a biosensor according to yet another embodiment of the present disclosure.

Referring to the figure, the biosensor 100c according to yet another embodiment of the present disclosure comprises a substrate 110; a source electrode 140a and a drain electrode 140b separated from each other on the substrate 110; a graphene layer 130 disposed on the substrate 110, and including one end connected to the source electrode 140a and the other end connected to the drain electrode 140b; a first doping layer 150a disposed on an area including one end of the graphene layer 130; a second doping layer 150b disposed on an area including the other end of the graphene layer 130 and separated from the first doping layer 150a; and a first passivation layer 160a and a second passivation layer 160b disposed on the first doping layer 150a and the second doping layer 150b, respectively.

Compared with the biosensor 100a of FIG. 4, the biosensor 100c of FIG. 6 is different in that the first doping layer 150a is formed in the L4c area on the graphene layer 130, where L4c area is smaller than L4 of FIG. 4; the second doping layer 150b is formed in the L5c area on the graphene layer 130, where L5c area is smaller than L5 of FIG. 4; and the open area of the graphene layer 130 is L3c, which is smaller than L3 of FIG. 4.

Meanwhile, as the length L3c of the third area PTc of the graphene layer 130 decreases, it is preferable that the height h3 of the graphene layer 130 is decreased, or the height h4c of the first doping layer 150a or the height h5c of the second doping layer 150b increases.

Accordingly, since the influence of the resistance component due to the area of the graphene layer 130 on which the first doping layer 150a is formed and the resistance component due to the area of the graphene layer 130 on which the second doping layer 150b is formed decreases, the conductivity of the graphene layer 130 may increase. As a result, the sensing sensitivity of a graphene-based sensor may be improved.

Throughout the document, preferred embodiments of the present disclosure have been described with reference to appended drawings; however, the present disclosure is not limited to the embodiments above. Rather, it should be noted that various modifications of the present disclosure may be made by those skilled in the art to which the present disclosure belongs without leaving the technical scope of the present disclosure defined by the appended claims, and these modifications should not be understood individually from the technical principles or perspectives of the present disclosure.

What is claimed is:
1. A biosensor comprising:
a substrate;

a source electrode and a drain electrode separated from each other on the substrate;

a graphene layer disposed on the substrate, and including one end connected to the source electrode and the other end connected to the drain electrode;

a first doping layer disposed on one end of the graphene layer;

a second doping layer disposed on the other end of the graphene layer and separated from the first doping layer;

a first passivation layer and a second passivation layer disposed on the first doping layer and the second doping layer, respectively; and a gate electrode disposed on top of either of the first passivation layer and the second passivation layer and separated from either of the first passivation layer and the second passivation layer, wherein the first doping layer is applied on the source electrode and one end of the graphene layer, and wherein the second doping layer is applied on the drain electrode and the other end of the graphene layer.

2. The biosensor of claim 1, wherein a portion of the graphene layer is applied by the first doping layer or the second doping layer and by the first passivation layer or the second passivation layer; and the other portion of the graphene layer is left open without being applied by the first doping layer or the second doping layer and by the first passivation layer or the second passivation layer.

3. The biosensor of claim 1, wherein the source electrode is formed on a first area which includes the one end of the graphene layer;

the first doping layer is formed on a second area adjacent to the first area of the graphene layer;

the first doping layer and the first passivation layer are not applied on a third area adjacent to the second area of the graphene layer;

the second doping layer is formed on a fourth area adjacent to the third area of the graphene layer; and the drain electrode is formed on a fifth area which includes the other end of the graphene layer and is adjacent to the fourth area.

4. The biosensor of claim 3, wherein a length of the second area or the fourth area of the graphene layer is shorter than a length of the third area.

5. The biosensor of claim 3, wherein a length of the second area or the fourth area of the graphene layer is less than or equal to 100 nm.

6. The biosensor of claim 3, wherein a length of the second area or the fourth area of the graphene layer is longer than a length of the first area or the fifth area of the graphene layer.

7. The biosensor of claim 3, wherein, as a resistance of the second area or the fourth area of the graphene layer decreases, a conductivity of the graphene layer increases.

8. The biosensor of claim 3, wherein, as a length of the third area of the graphene layer increases, a conductivity of the graphene layer increases.

9. The biosensor of claim 3, wherein, as a ratio of a length of the second area or the fourth area of the graphene layer to a length of the third area of the graphene layer decreases, a conductivity of the graphene layer increases.

10. The biosensor of claim 3, wherein a height of the graphene layer is less than a height of the substrate.

11. The biosensor of claim 3, wherein, as a length of the third area of the graphene layer decreases, a height of the graphene layer decreases or a height of the first doping layer or a height of the second doping layer increases.

12. The biosensor of claim 1, wherein the first doping layer or the second doping layer includes an organic compound or an inorganic compound, and the inorganic compound includes at least one of WO3, MoO3, or ZnO.

13. The biosensor of claim 1, further comprising an insulating layer disposed on the substrate, wherein the source electrode, the drain electrode, and the graphene layer are disposed on the insulating layer.

14. A biosensor comprising:

a substrate;

a source electrode and a drain electrode separated from each other on the substrate;

a graphene layer disposed on the substrate, and including one end connected to the source electrode and the other end connected to the drain electrode;

a first doping layer and a second doping layer applied on a portion of the graphene layer and separated from each other thereon;

a first passivation layer and a second passivation layer disposed on the first doping layer and the second doping layer, respectively; and a gate electrode disposed on top of either of the first passivation layer and the second passivation layer and separated from either of the first passivation layer and the second passivation layer, wherein the first doping layer is applied on the source electrode and one end of the graphene layer, and wherein the second doping layer is applied on the drain electrode and the other end of the graphene layer.

15. The biosensor of claim 1, wherein the first doping layer is applied directly on a top surface of the source electrode and directly on a top surface of one end of the graphene layer, and the second doping layer is applied directly on a top surface of the drain electrode and directly on a top surface of the other end of the graphene layer.

16. The biosensor of claim 1, wherein the first doping layer directly contacts both the source electrode and graphene layer, and the second doping layer directly contacts the drain electrode and the graphene layer.

17. The biosensor of claim 1, wherein the first doping layer is disposed directly between the source electrode and the first passivation layer, and the second doping layer is disposed directly between the drain electrode and the second passivation layer.

18. The biosensor of claim 1, wherein the first doping layer comprises a step shape to directly contact the one end of the graphene layer, wherein the second doping layer comprises a step shape and directly contacts the other end of the graphene layer, wherein the one end of the graphene layer extends passed the step shape of the first doping layer, and wherein the other end of the graphene layer extends passed the step shape of the second doping layer.

\* \* \* \* \*